United States Patent
Miyamura et al.

(10) Patent No.: US 9,604,918 B2
(45) Date of Patent: Mar. 28, 2017

(54) CARBOXYLIC ACID ESTER/CARBAMATE COMPOUND WITH POLYMERIZABLE FUNCTIONAL GROUP AND FLUORINE ATOM GROUP, AND MANUFACTURING METHOD THEREFOR

(71) Applicant: UNIMATEC CO., LTD., Tokyo (JP)

(72) Inventors: Takuhiro Miyamura, Ibaraki (JP); Keisuke Kokinn, Ibaraki (JP); Sunao Ikeda, Ibaraki (JP)

(73) Assignee: UNIMATEC CO., LTD., Tokyo (JP)

( * ) Notice: Subject to any disclaimer, the term of this patent is extended or adjusted under 35 U.S.C. 154(b) by 0 days.

(21) Appl. No.: 14/910,815

(22) PCT Filed: Mar. 20, 2015

(86) PCT No.: PCT/JP2015/058619
§ 371 (c)(1),
(2) Date: Feb. 8, 2016

(87) PCT Pub. No.: WO2015/151885
PCT Pub. Date: Oct. 8, 2015

(65) Prior Publication Data
US 2016/0185714 A1 Jun. 30, 2016

(30) Foreign Application Priority Data
Apr. 4, 2014 (JP) .................. 2014-078190

(51) Int. Cl.
| | | |
|---|---|---|
| *C07C 271/16* | (2006.01) | |
| *C07C 269/02* | (2006.01) | |
| *C07C 269/06* | (2006.01) | |
| *C08F 20/34* | (2006.01) | |
| *C08F 20/24* | (2006.01) | |

(52) U.S. Cl.
CPC .......... *C07C 271/16* (2013.01); *C07C 269/02* (2013.01); *C07C 269/06* (2013.01); *C08F 20/24* (2013.01); *C08F 20/34* (2013.01); *C07C 2101/14* (2013.01)

(58) Field of Classification Search
CPC ... C07C 271/16; C07C 269/02; C07C 269/06; C07C 2101/14; C08F 20/24; C08F 20/34
USPC .......................................... 558/283
See application file for complete search history.

(56) References Cited

U.S. PATENT DOCUMENTS 5,965,659 A * 10/1999 Kubo .................... C08L 51/003
524/504

FOREIGN PATENT DOCUMENTS

| CN | 102002129 A | 4/2011 |
| JP | 58-194839 A | 11/1983 |
| KR | 10-2012-0104850 A | 9/2012 |
| WO | WO 95/18194 | 7/1995 |

OTHER PUBLICATIONS

International Search Report & Written Opinion dated Jun. 2, 2015 corresponding to International Patent Application No. PCT/JP2015/058619, and English translation thereof.

* cited by examiner

*Primary Examiner* — Kristin Vajda
(74) *Attorney, Agent, or Firm* — Squire Patton Boggs (US) LLP

(57) ABSTRACT

Provided are a fluorine-containing monomer soluble in a hydrocarbon-based solvent as well as excellent in water and oil repellence, and a manufacturing method therefor. The fluorine-containing monomer is a carboxylic acid ester/carbamate compound having a polymerizable functional group and a fluorine atom group, and represented by the following general formula: $C_aF_{2a+1}O-(C_bF_{2b}O)_c-C_2F_4COO-Z-(CONHR)_d$. The method for manufacturing the carboxylic acid ester/carbamate compound is comprised of the steps of making an isocyanate compound having a polymerizable functional group react with an alcohol such as a polyalkylene glycol, a cycloalkane dimethanol, or a polyhydric alcohol to produce a hydroxycarbamate, and subsequently making the resulting hydroxycarbamate react with a perfluoropolyether carboxylic acid halide.

6 Claims, No Drawings

CARBOXYLIC ACID ESTER/CARBAMATE COMPOUND WITH POLYMERIZABLE FUNCTIONAL GROUP AND FLUORINE ATOM GROUP, AND MANUFACTURING METHOD THEREFOR

TECHNICAL FIELD

The present invention relates to a carboxylic acid ester/carbamate compound having a polymerizable functional group and a fluorine atom group, and a method for manufacturing the compound.

BACKGROUND ART

Compounds with a fluorine atom in a molecule have, in general, excellent thermal and chemical stability as well as good optical and surface active properties. In view of this, compounds with a fluorine atom in a molecule are applied to various products such as an antireflection film for a monitor screen, a cladding material for an optical fiber, and a coating agent.

Examples of the compounds with a fluorine atom in a molecule include a fluorine-containing ester monomer and a fluorine-containing ether monomer. A homopolymer and a copolymer having various chemical structures obtained via those monomers have been developed and used for the above applications.

Patent Literature 1 discloses a fluorine-containing acrylic acid ester represented by the following general formula, as a representative example of a fluorine-containing ester monomer.

[Chemical Formula 1]

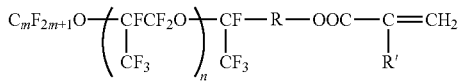

In the formula, R is a divalent organic linking group; R' is hydrogen or methyl; n is 0 or a positive integer; and m is a positive integer.

CITATION LIST

Patent Literature

Patent Literature 1: Japanese Unexamined Patent Application Publication No. Sho 58-194839A

SUMMARY OF THE INVENTION

Technical Problem

Meanwhile, such fluorine-containing monomers are not soluble in an inexpensive hydrocarbon-based solvent but soluble only in a fluorine-based solvent. This causes a drawback that use of those fluorine-containing monomers is restricted in view of cost and legal control.

In fact, the fluorine-containing monomer disclosed in Patent Literature 1 exhibits water and oil repellence, but is insoluble in a common solvent. Thereby, a drawback is that a phase separation occurs when the fluorine-containing monomer is mixed with other resins.

The present invention has been made in view of the above drawbacks. Specifically, a purpose of the present invention is to provide a fluorine-containing monomer soluble in a hydrocarbon-based solvent as well as excellent in water and oil repellence, and a method for manufacturing the fluorine-containing monomer.

Solution to Problem

The present inventors have investigated introducing various hydrocarbon groups into a monomer having a fluorine atom group (i.e., a functional group having a plurality of fluorine atoms) and a polymerizable functional group in order to increase solubility of the fluorine-containing monomer in a hydrocarbon-based solvent. Further, the present inventors have investigated a chemical structure of the fluorine atom group and a bond type of the respective functional groups, etc. As a result, the present inventors have found out that a fluorine-containing monomer having a specific chemical structure made by introducing a hydrocarbon group of a polyether or cycloaliphatic linker between the fluorine atom group and the polymerizable functional group in the monomer demonstrates excellent solubility in a hydrocarbon-based solvent and miscibility with a curable resin.

Accordingly, the present invention is realized through the intensive research. Specifically, the present invention includes the following aspects.

A carboxylic acid ester/carbamate compound according to the present invention is a fluorine-containing monomer represented by general formula [I] having a polymerizable functional group and a fluorine atom group.

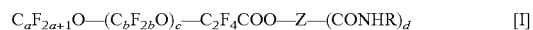

In general formula [I], a is an integer of 1 to 3; b is an integer of 1 to 4; c is an integer of 0 to 50; d is an integer of 1 to 3;

Z is a divalent to tetravalent organic linking group derived from a peroxide-free alcohol represented by $-(C_eH_{2e}O)_f-$, $-CH_2(\text{cyclo-}C_gH_{2g-2})CH_2O-$, or $-C_hH_{2h+1-i}O_i-$;

e is an integer of 1 to 6; f is an integer of 1 to 12; g is an integer of 3 to 6; h is an integer of 2 to 12; i is an integer of 1 to 3; and R is a polymerizable functional group represented by the following general formula [II]:

In general formula [II], $R^1$ is hydrogen or methyl; $R^2$ is hydrogen or $CH_2=CHCOOCH_2-$; and $R^3$ is hydrogen or methyl.

A method for manufacturing a carboxylic acid ester/carbamate compound according to the present invention is carried out by the following steps. First, an isocyanate compound represented by general formula [IV] having a polymerizable functional group is made to react with an alcohol such as a polyalkylene glycol represented by general formula [III-1], a cycloalkane dimethanol represented by general formula [III-2], or a linear or branched polyhydric alcohol represented by general formula [III-3] to produce a hydroxycarbamate represented by general formula [V-1], [V-2], or [V-3]. Then, the resulting hydroxycarbamate is made to react with a perfluoropolyether carboxylic acid halide represented by general formula [VI].

In general formulae [III-1]-[III-3], e is an integer of 1 to 6; f is an integer of 1 to 12; g is an integer of 3 to 6; h is an integer of 2 to 12; i is an integer of 1 to 3.

$$H_2C=C(R^1)COOCH_2CR^2R^3-NCO \qquad [IV]$$

In general formula [IV], $R^1$ is hydrogen or methyl; $R^2$ is hydrogen or $CH_2=CHCOOCH_2-$; and $R^3$ is hydrogen or methyl.

$$HO(C_eH_{2e}O)_fCONHR \qquad [V-1],$$

$$HOCH_2(cyclo\text{-}C_gH_{2g-2})CH_2OCONHR \qquad [V-2]$$

$$HOC_hH_{2h+1-i}(OCONHR)_i \qquad [V-3],$$

In general formulae [V-1]-[V-3], e is an integer of 1 to 6; f is an integer of 1 to 12; g is an integer of 3 to 6; h is an integer of 2 to 12; i is an integer of 1 to 3; and R is a polymerizable functional group represented by the following general formula [II]:

$$H_2C=C(R^1OCOOCH_2CR^2R^3- \qquad [II]$$

In general formula [II], $R^1$ is hydrogen or methyl; $R^2$ is hydrogen or $CH_2=CHCOOCH_2-$; and $R^3$ is hydrogen or methyl.

$$C_aF_{2a+1}O-(C_bF_{2b}O)_c-C_2F_4CO-X \qquad [VI]$$

In general formula [VI], X is a halogen atom; a is an integer of 1 to 3; b is an integer of 1 to 4; and c is an integer of 0 to 50.

Advantageous Effects of Invention

The fluorine-containing monomer according to the present invention is soluble in a hydrocarbon-based solvent and excellent in water and oil repellence. In addition, the method for manufacturing the fluorine-containing monomer according to the present invention gives the product via simple steps in a high yield.

EMBODIMENTS FOR CARRYING OUT INVENTION

Hereinafter, embodiments of the present invention will be described in detail. The present invention, however, is not limited to these specific embodiments illustrated below.

The method for manufacturing a carboxylic acid ester/carbamate according to the present invention is carried out by the steps of making an isocyanate having a polymerizable functional group react with an alcohol such as a polyalkylene glycol, a cycloalkane dimethanol, or a polyhydric alcohol, and subsequently making the resulting intermediate react with an acid halide having a perfluoropolyether group.

More specifically, the method is carried out by the step of making an isocyanate such as an isocyanatoalkylacrylate, an isocyanatoalkyl methacrylate, or a bis(acryloyloxymethynalkyl isocyanate react with an alcohol such as a polyalkylene glycol, a cycloalkane dimethanol, or a polyhydric alcohol under the presence of a catalyst. Subsequently, the method is further carried out by the step of making the resulting intermediate react with an acid halide having a perfluoroether group under the presence of a hydrogen halide scavenger, thereby to produce a fluorine-containing polymerizable monomer.

Next, the former reaction step will be described in detail.

The former reaction step is carried out by making an isocyanate compound represented by general formula [IV] having a polymerizable functional group react with an alcohol compound such as a polyalkylene glycol represented by general formula [III-1], a cycloalkane dimethanol represented by general formula [III-2], or a polyhydric alcohol represented by general formula [III-3] so as to produce a hydroxycarbamate represented by general formula [V-1], [V-2], or [V-3].

The polyalkylene glycol is represented by the following general formula [III-1]:

$$HO(C_eH_{2e}O)_fH \qquad [III-1]$$

In general formula [III-1], e is an integer of 1 to 6; and f is an integer of 1 to 12.

Further, the cycloalkane dimethanol is represented by the following general formula [III-2]:

$$HOCH_2(cyclo\text{-}C_gH_{2g-2})CH_2OH \qquad [III-2]$$

In general formula [III-2], g is an integer of 3 to 6.

Moreover, the polyhydric alcohol is represented by the following general formula [III-3];

$$HOC_hH_{2h+1-i}(OH)_i \qquad [III-3]$$

In general formula [III-3], h is an integer of 2 to 12; and i is an integer of 1 to 3. The carbon chain of the polyhydric alcohol may be linear or branched. Note the bonding position of the hydroxyl group is not limited, and the polyhydric alcohol is free from a peroxide.

Examples of the polyalkylene glycol used include ethylene glycol, diethylene glycol, triethylene glycol, polyethylene glycol, propylene glycol, dipropylene glycol, tripropylene glycol, and polypropylene glycol.

Examples of the cycloalkane dimethanol used include cyclopropane dimethanol, cyclobutane dimethanol, cyclopentane dimethanol, and cyclohexane dimethanol.

The bonding position of a hydroxyl group at the linear or branched polyhydric alcohol used is not limited. Examples of the polyhydric alcohol used include ethanediol, propanediol, butanediol, pentanediol, hexanediol, heptanediol, octanediol, nonanediol, decanediol, undecanediol, dodecanediol, propanetriol, butanetriol, pentanetriol, hexanetriol, heptanetriol, octanetriol, nonanetriol, decanetriol, undecanetriol, dodecanetriol, butanetetraol, pentanetetraol, hexanetetraol, heptanetetraol, octanetetraol, nonanetetraol, decanetetraol, undecanetetraol, dodecanetetraol, and pentaerythritol.

The isocyanate compound having a polymerizable functional group is represented by the following general formula [IV];

$$H_2C=C(R^1)COOCH_2CR^2R^3-NCO \qquad [IV]$$

In the general formula [IV], $R^1$ is hydrogen or methyl; $R^2$ is hydrogen or $CH_2=CHCOOCH_2-$; and $R^3$ is hydrogen or methyl.

Examples of the isocyanate compound having a polymerizable functional group include an isocyanatoalkyl acrylate, an isocyanatoalkyl methacrylate, and a bis(acryloyloxymethyl)alkyl isocyanate. Specific examples used include isocyanatomethyl acrylate, isocyanatoethyl acrylate, isocyanatopropyl acrylate, isocyanatomethyl methacrylate, isocyanatoethyl methacrylate, isocyanatopropyl methacrylate, bis(acryloyloxymethyl)methyl isocyanate, bis(acryloyloxymethyl)ethyl isocyanate, and bis(acryloyloxymethyl)propyl isocyanate. In view of availability, particularly preferred are isocyanatoethyl acrylate (Karenz AOI, manufactured by SHOWA DENKO K.K.), isocyanatoethyl methacrylate (Karenz MOI, manufactured by SHOWA DENKO K.K.), and 1, 1-bis(acryloyloxymethyl)ethyl isocyanate (Karenz BEI, manufactured by SHOWA DENKO K.K.).

Karenz AOI: H₂C=CHCOOCH₂CH₂NCO

Karenz MOI: H₂C=C(CH₃)COOCH₂CH₂NCO

Karenz BEI: (H₂C=CHCOOCH₂)₂C(CH₃)NCO

Usually, 1 to 1.5-fold mol equivalent 1 of the isocyanate compound such as an isocyanatoalkyl (di)(meth)acrylate is used per (the total number of hydroxyl groups—1) mol of the alcohol represented by the general formula [III-1], [III-2], or [III-3]. A solvent may or may not be used. When a solvent is employed, an aromatic, ketone, or ether type solvent is used. Preferred are toluene, methyl isobutyl ketone, and dibutyl ether, etc. The reaction temperature is not particularly limited. However, in view of controllability and prevention of causing undesirable polymerization in a reaction mixture, the reaction temperature is preferably set in the range from room temperature to about 60° C.

Further, when the isocyanate compound is made to react with the polyalkylene glycol, cycloalkane dimethanol, or polyalkylene glycol, an organometallic catalyst or a basic catalyst is preferably used so as to promote the reaction smoothly. Examples of the organometallic catalyst used include dibutyltin dilaurate, tin octylate, and lead naphthenate. Examples of the basic catalyst used include 1,8-diazabicyclo[5.4.0]undeca-7-en, 1,4-diazabicyclo[2.2.2]octane, bis[(2-dimethylamino)ethyl]ether, and 1,1,6,6-tetramethyl hexane diamine. Preferred are an organometallic tin derivative such as dibutyltin dilaurate and a nitrogen-containing heterocyclic derivative such as 1,8-diazabicyclo[5.4.0]undeca-7-en.

Accordingly, the reaction of the isocyanate compound with the polyalkylene glycol, cycloalkane dimethanol, or polyhydric alcohol produces a hydroxycarbamate as an intermediate material.

The hydroxycarbamate is represented by the following general formula [V-1], [V-2], or [V-3]:

HO(C_eH_{2e}O)_fCONHR     [V-1],

HOCH₂(cyclo-C_gH_{2g-2})CH₂OCONHR     [V-2],

HOC_hH_{2h+1-i}(OCONHR)_i     [V3]

In general formulae [V-1] to [V-3], e is an integer of 1 to 6; f is an integer of 1 to 12; g is an integer of 3 to 6; h is an integer of 2 to 12; i is an integer of 1 to 3; and R is a polymerizable functional group represented by the following general formula [II]:

H₂C=C(R¹)COOCH₂CR²R³—     [II]

In general formula [II], R¹ is hydrogen or methyl; R² is hydrogen or CH₂=CHCOOCH₂—; and R³ is hydrogen or methyl.

Next, the latter reaction step will be described in detail.

The latter reaction step is carried out by making the above hydroxycarbamate react with a perfluoropolyether carboxylic acid halide represented by general formula [VI], thereby to produce a carboxylic acid ester/carbamate compound.

The perfluoropolyether carboxylic acid halide is represented by the following general formula [VI]:

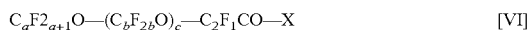

C_aF_{2a+1}O—(C_bF_{2b}O)_c—C₂F₁CO—X     [VI]

In general formula [VI], X is a halogen atom; a is an integer of 1 to 3; b is an integer of 1 to 4; and c is an integer of 0 to 50.

Specific examples of the perfluoropolyether carboxylic acid halide used include:

(a) 2,4,4,5,7,7,8,10,10,11,13,13,14,16,16,17,17,18,18,18-eicosafluoro-3,6,9,12,15-pentaoxa-2,5,8,11,14-pentakis(trifluoromethyl)octadecanoyl fluoride;

(b) 2,4,4,5,7,7,8,10,10,11,13,13,14,16,16,17,17,17-octadecafluoro-3,6,9,12,15-pentaoxa-2,5,8,11,14-pentakis(trifluoromethyl)pheptadecanoyl fluoride;

(c) 2,4,4,5,7,7,8,10,10,11,13,13,14,16,16,16-hexadecafluoro-3,6,9,12,15-pentaoxa-2,5,8,11,14-pentakis(trifluoromethyl)hexadecanoyl fluoride;

(d) 2,4,4,5,7,7,8,10,10,11,13,13,14,16,16,17,19,19,20,22,22,23,25,25,26,28,28,29,29,30,30,30-dotriacontafluoro3,6,9,12,15,18,21,24,27 -nonaoxa-2,5,8,11,14,17,20,23,26-nonakis(trifluoromethyl)triacontanoyl fluoride;

(e) 2,4,4,5,7,7,8,10,10,11,13,13,14,16,16,17,19,19,20,22,22,23,25,25,26,28,28,29,29,29-triacontafluoro-3,6,9,12,15,18,21,24,27-nonaoxa-2,5,8,11,14,17,20,23,26-nonakis(trifluoromethyl)nonacosanoyl fluoride;

(f) 2,4,4,5,7,7,8,10,10,11,13,13,14,16,16,17,19,19,20,22,22,23,25,25,26,28,28,28octacosafluoro-3,6,9,12,15,18,21,24,27-nonaoxa-2,5,8,11,14,17,20,23,26-nonakis(trifluoromethyl)octacosanoyl fluoride;

(g) 2,2,3,3,5,5,6,6,7,7,9,9,10,10,11,11,13,13,14,14,15,15,15-tricosafluoro-4,8,12-trioxapentadecanoyl fluoride; and (h) 2,2,3,3,5,5,6,6,7,7,9,9,10,10,11,11,13,13,14,14,15,15,17,17,18,18,19,19,21,21,22,22,23,23,25,25,26,26,27,27,29,29,30,30,31,31,31-heptatetracontafluoro-4,8,12,16,20,24,28-heptaoxahentriacontanoyl fluoride.

Among them, preferred are: (a) 2,4,4,5,7,7,8,10,10,11,13,13,14,16,16,17,17,18,18,18-eicosafluoro-3,6,9,12,15-pentaoxa-2,5,8,11,14-pentakis(trifluoromethyl)poctadecanoyl fluoride; and (d) 2,4,4,5,7,7,8,10,10,11,13,13,14,16,16,17,19,19,20,22,22,23,25,25,26,28,28,29,29,30,30,30-dotriacontafluoro-3,6,9,12,15,18,21,24,27-nonaoxa-2,5,8,11,14,17,20,23,26-nonakis(trifluoromethyl)triacontanoyl fluoride; and the like.

The chemical formulae of the above perfluoropolyether carboxylic acid halide are illustrated as follows.

[Chemical Formulae 2]

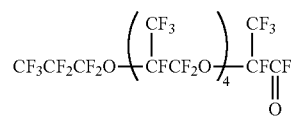
(a)

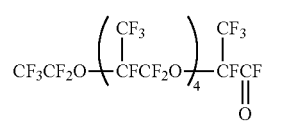
(b)

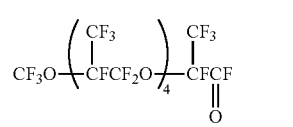
(c)

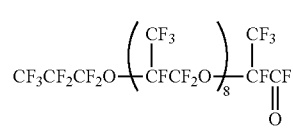
(d)

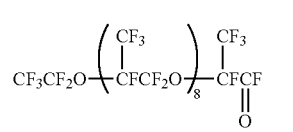
(e)

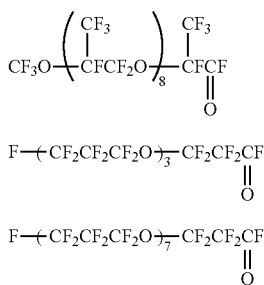

(f)

F—(CF$_2$CF$_2$CF$_2$O)$_{\overline{3}}$—CF$_2$CF$_2$CF
‖
O (g)

F—(CF$_2$CF$_2$CF$_2$O)$_{\overline{7}}$—CF$_2$CF$_2$CF
‖
O (h)

The reaction of the hydroxycarbamate with the perfluoropolyether carboxylic acid halide is carried out via a dehydrohalogenation reaction. That is, 1.1 to 2-fold mol equivalent of the hydroxycarbamate [i.e. hydroxyl group-containing (di)(meth)acrylate] is usually used per mol of the perfluoropolyether-containing acid halide.

Any of a reaction solvent may be used as long as the reaction solvent is inert in this reaction. Fluorine-based solvents, in general, may be used. Specific examples include ASAHICLEAN AK-225 (manufactured by ASAHI GLASS CO., LTD.), ASAHICLEAN AE-3000 (manufactured by ASAHI GLASS CO., LTD.), Novec HFE (manufactured by Sumitomo 3M Limited), Vertrel XF (manufactured by Du Pont Kabushiki Kaisha), and Fluorinert FC-72 (manufactured by Sumitomo 3M Limited). Preferred is ASAHI-CLEAN AK-225 (manufactured by ASAHI GLASS CO., LTD.).

The dehydrohalogenation reaction is preferably carried out under the presence of a hydrogen halide scavenger. Examples of the hydrogen halide scavenger generally used include: alkali metal fluorides such as lithium fluoride, sodium fluoride, and potassium fluoride; and organic amine compounds such as triethylamine and tributylamine. Among them, preferred are an alkali metal fluoride (e.g., sodium fluoride) and triethylamine in view of the cost and capacity of capturing generated hydrogen fluoride. The molar ratio of the hydrogen halide scavenger to the perfluoropolyether carboxylic acid halide is ranged from 2 to 8 and preferably from 2.1 to 3.0.

The resulting carboxylic acid ester/carbamate has a polymerizable functional group. Therefore, methoquinone (i.e. p-methoxyphenol) or hydroquinone is preferably added, as a polymerization inhibitor, to the reaction mixture to carry out the reaction.

Examples of the carboxylic acid ester/carbamate, as so synthesized, according to the present invention include the following compounds.

[Chemical Formulae 3]

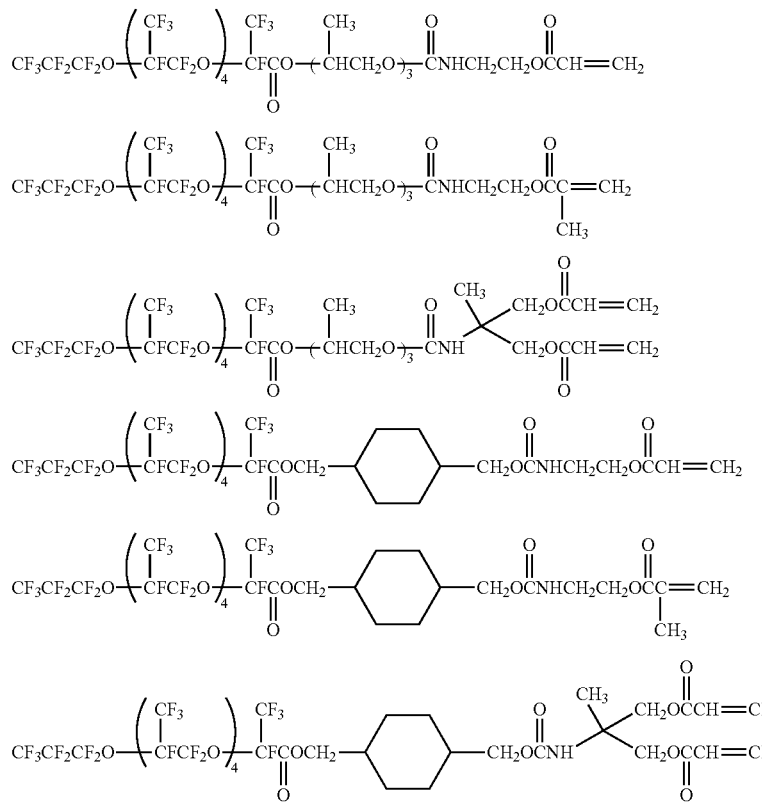

[Chemical Formulae 4]

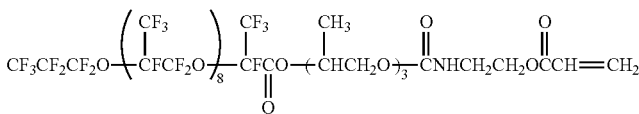

-continued
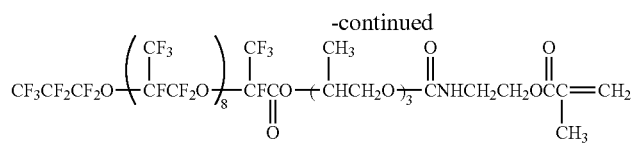
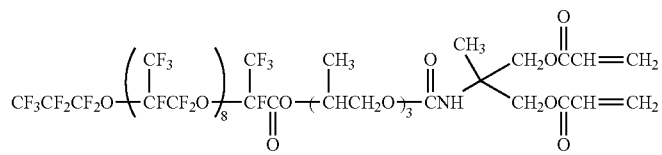
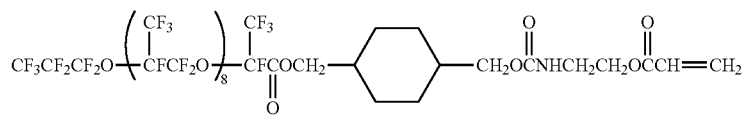
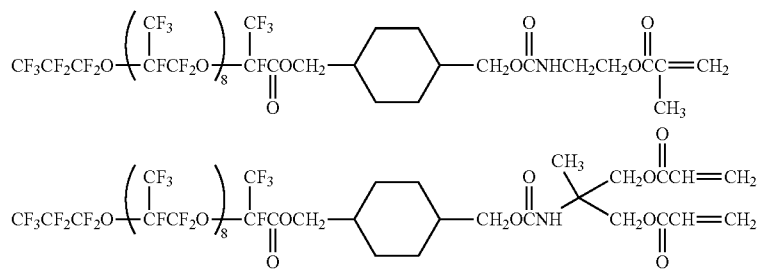
[Chemical Formulae 5]
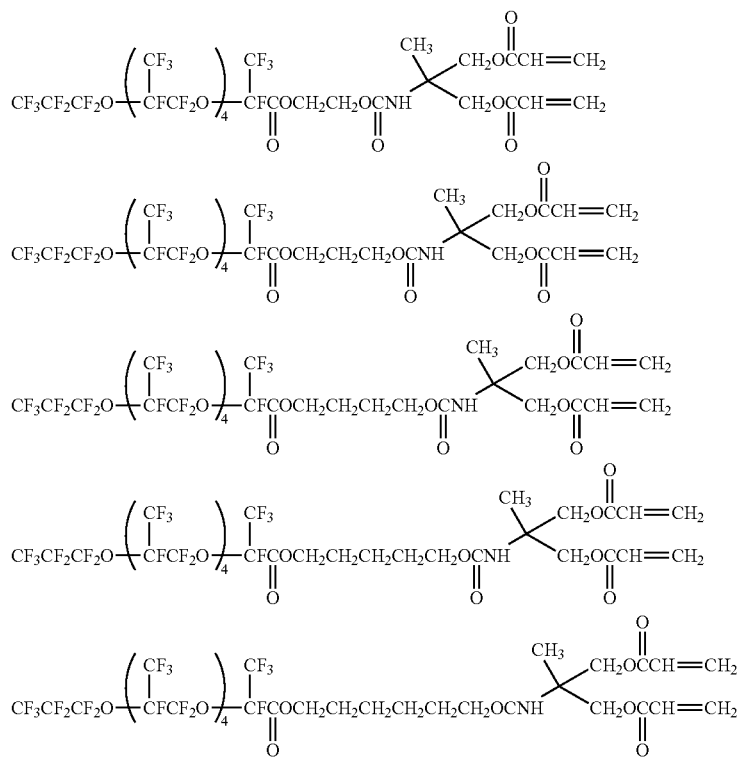

[Chemical Formulae 6]
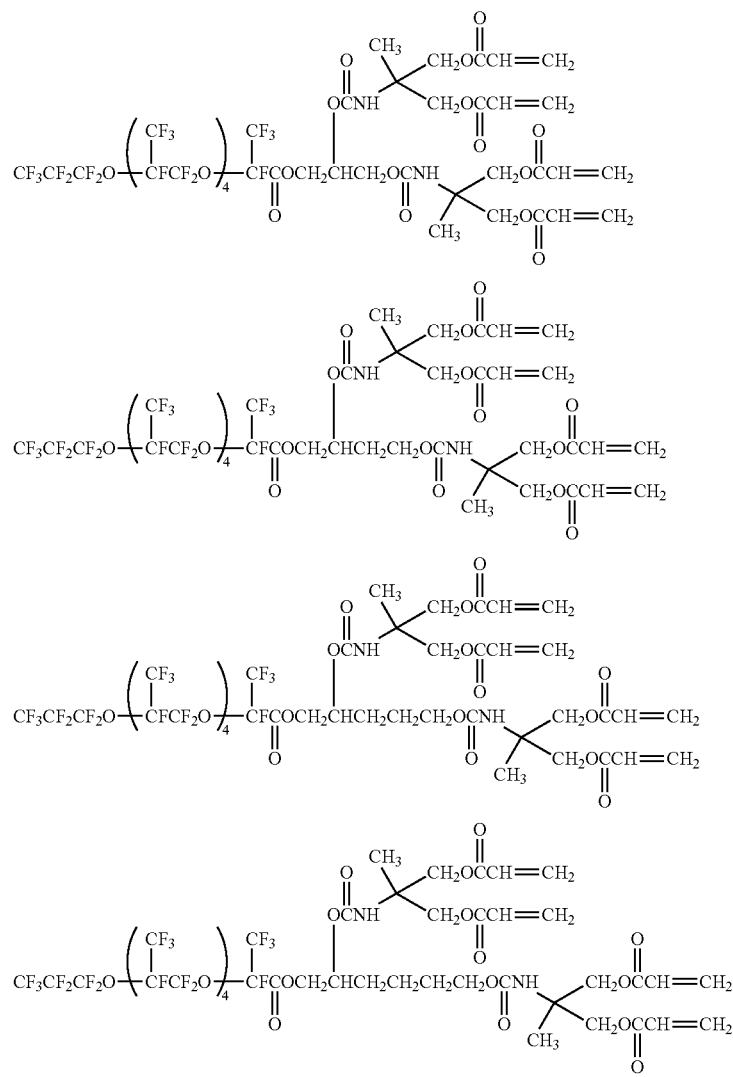
[Chemical Formulae 7]
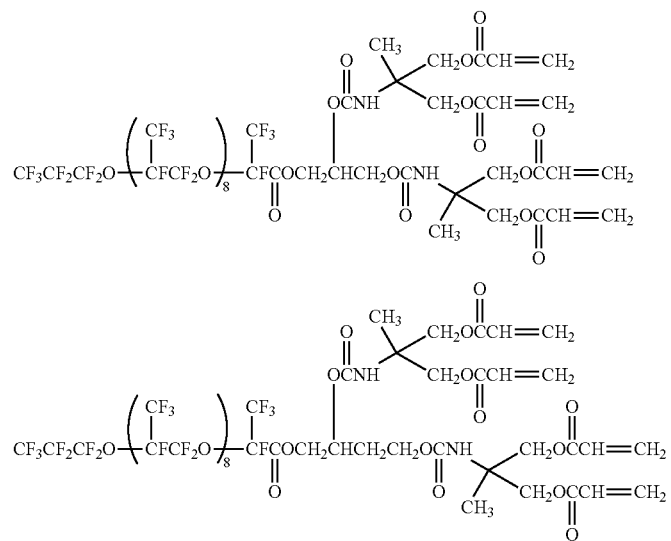

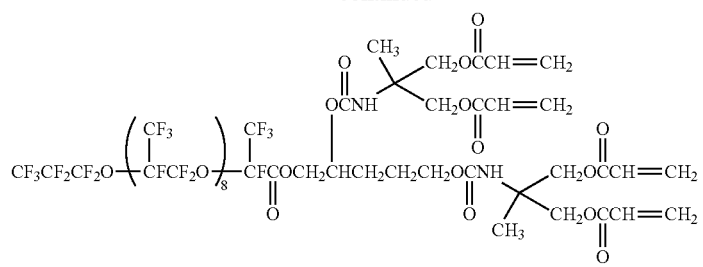
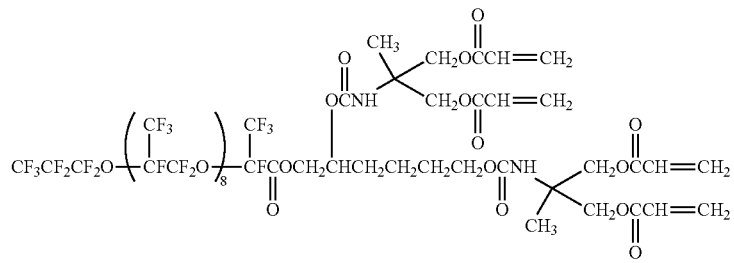
[Chemical Formulae 8]
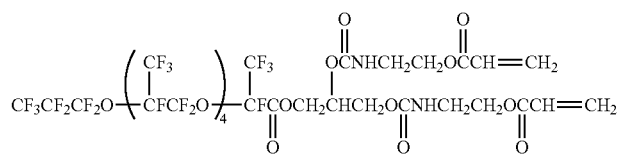
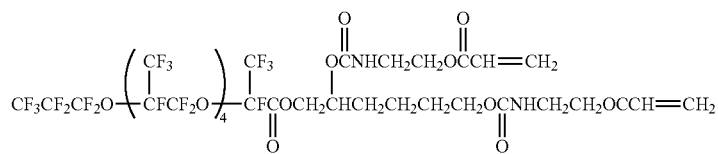
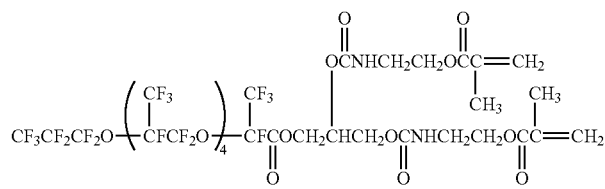
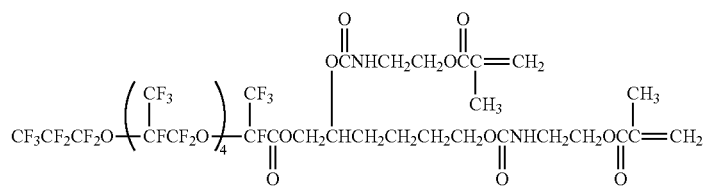
[Chemical Formulae 9]
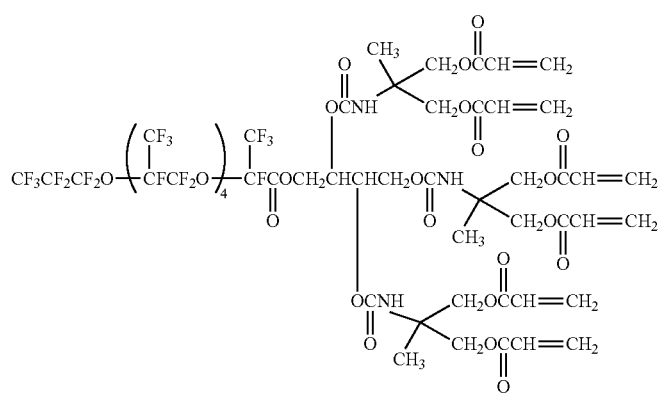

-continued

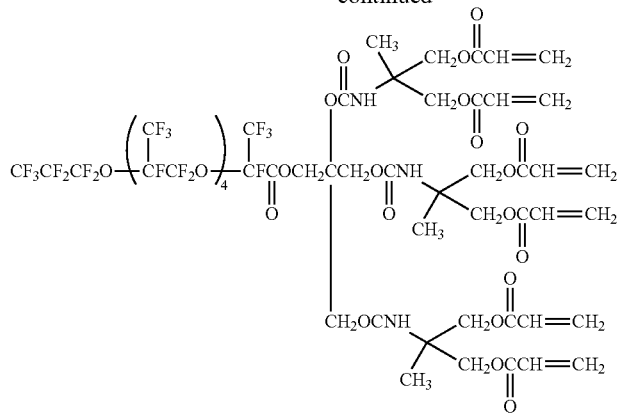

The carboxylic acid ester/carbamate according to the present invention is a fluorine-containing polyether (di) (meth)acrylate, which has a polymerizable functional group, a fluorine atom group, and a hydrocarbon group in a molecule. This structural feature enables the carboxylic acid ester/carbamate to exhibit excellent solubility into a common solvent and miscibility with a curable resin without deteriorating water repellence, oil repellence, fingerprint resistance, and antifouling effects. Further, many fluorine atoms included in a molecule of the carboxylic acid ester/carbamate give the carboxylic acid ester/carbamate excellent thermal and chemical stability as well as good optical and surface active properties.

Moreover, the carboxylic acid ester/carbamate according to the present invention is cured by energy beams such as visible light, UV light, and electron beams. Thus, the carboxylic acid ester/carbamate is applicable to light-sensitive curable inks, coating materials, and electron beam-curable adhesives. Furthermore, the carboxylic acid ester/carbamate may be synthesized as a multifunctional monomer, and such a multifunctional monomer can perform three-dimensional cross linking. In this case, the carboxylic acid ester/carbamate can be used as, for example, cross-linkers and/or improvers for various resins. This enables physical properties of the resins such as hardness, strength, thermal resistance, weather resistance, and chemical resistance to be enhanced and improved.

A high content of fluorine in a molecule gives the carboxylic acid ester/carbamate according to the present invention a low refractive index. Accordingly, the carboxylic acid ester/carbamate can be used for an antireflection film of a display and a cladding material of an optical fiber, etc.

Further, the surface active properties enable the carboxylic acid ester/carbamate to be used for various coating agents for mold release, surface modifiers, and water and oil repellents, etc.

EXAMPLES

Hereinafter, Examples will be illustrated in detail. The present invention, however, is not limited to those Examples.

Example 1

To 200 g of toluene, were added 307.6 g (1.60 mol) of tripropylene glycol and 1.01 g of dibutyltin dilaurate (DBTDL). Next, 430.8 g (1.80 mol) of 1, 1-bis(acryloyloxymethyl)ethyl isocyanate was added dropwise to the reaction mixture while stirring, and the mixture was stirred for 5 hours. After checking elimination of 1, 1-bis(acryloyloxymethyl)ethyl isocyanate by gas chromatography (GC), the reaction was terminated. The obtained amount of the product was 637.2 g (92.3% yield).

Then, 164.4 g (0.381 mol) of the isolated product was dissolved in 300 g of a mixed solvent of HCFC-225ca/HCFC-225cb (ASAHICLEAN AK-225, manufactured by ASAHI GLASS CO., LTD.). After that, 44.1 g (1.05 mol) of NaF was added. Subsequently, 350 g (0.351 mol) of a fluorine-containing polyether acid fluoride was added dropwise to the reaction mixture while stirring, and the mixture was stirred for 2 hours. After checking elimination of a peak of the acid fluoride by NMR, the reaction was terminated. The obtained amount of the product was 440.2 g (89.1% yield), and the purity was 95.6%.

The reactions in Example 1 involve the following two chemical equations.

[Chemical Equation 10]

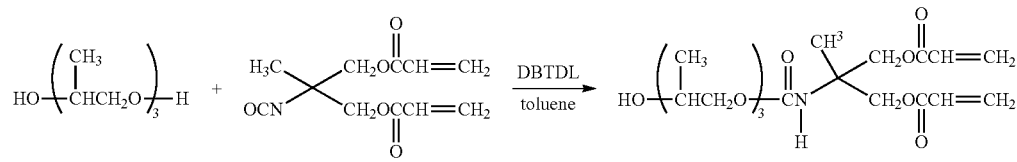

[Chemical Equation 11]

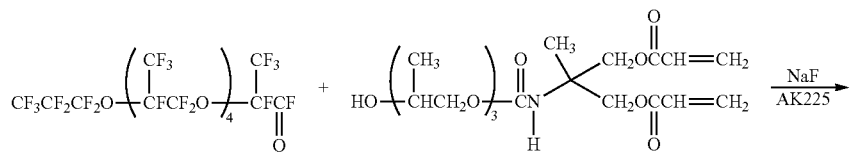

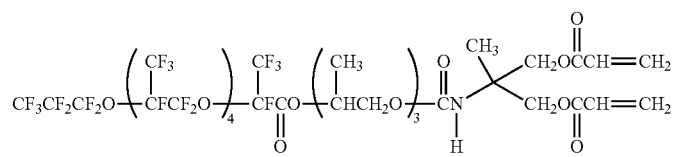

The identification results of NMR with respect to the product of Example 1 are described below. It was demonstrated that the above reactions of Example 1 yielded a carboxylic acid ester/carbamate having the following chemical formula.

[Chemical Formula 12]

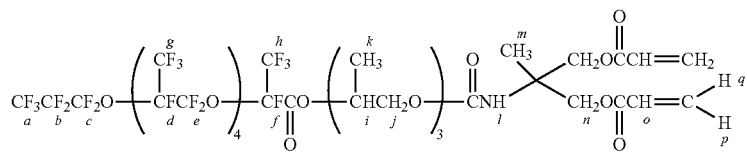

$^{19}$F-NMR[$(CD_3)_2CO$, $C_6F_6$] δ (ppm): −143.8: d, −130.2: f, −128.7: b, −81.4: c, −80.6: e, −79.1: a, g, h.

$^{1}$H-NMR[$(CD_3)_2CO$] δ (ppm): 1.0 to 1.4: k, 1.4: m, 3.5 to 4.1: i, j, 4.4: n, 5.9: q, 6.2: p, 6.4: o.

Example 2

To 200 g of toluene, were added 225.9 g (1.60 mol) of cyclohexane dimethanol and 1.01 g of dibutyltin dilaurate (DBTDL). Next, 279.3 g (1.80 mol) of isocyanatoethyl methacrylate was added dropwise to the reaction mixture while stirring, and the mixture was stirred for 5 hours. After checking elimination of isocyanatoethyl methaacrylate by GC, the reaction was terminated. The obtained amount was 431.8 g (90.1% yield).

Then, 113.8 g (0.380 mol) of the isolated product was dissolved in 300 g of a mixed solvent of HCFC-225ca/HCFC-225cb (ASAHICLEAN AK-225, manufactured by ASAHI GLASS CO., LTD.). After that, 44.1 g (1.05 mol) of NaF was added. Subsequently, 350 g (0.351 mol) of a fluorine-containing polyether acid fluoride was added dropwise to the reaction mixture while stirring, and the mixture was stirred for 2 hours. After checking elimination of a peak of the acid fluoride by NMR, the reaction was terminated. The obtained amount of the product was 399.5 g (88.4% yield), and the purity was 96.7%.

The reactions in Example 2 involve the following two chemical equations.

[Chemical Equation 13]

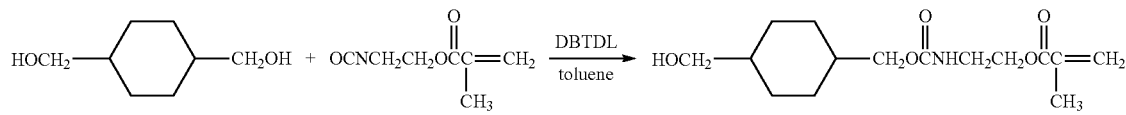

[Chemical Equation 14]

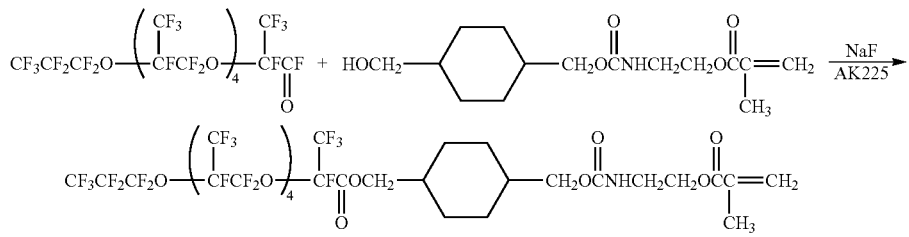

The identification results of NMR with respect to the product of Example 2 are described below. It was demonstrated that the above reactions of Example 2 yielded a carboxylic acid ester/carbamate having the following chemical formula.

[Chemical Equation 15]

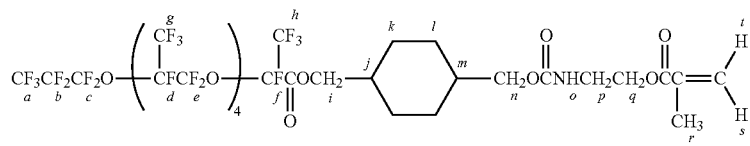

$^{19}$F-NMR[(CD$_3$)$_2$CO, C$_6$F$_6$] δ (ppm): −143.5: d, −130.0: f, −128.9: b, −82.5 to −76.4: a, c, e, g, h.
$^1$H-NMR[(CD$_3$)$_2$CO] δ (ppm): 0.95 to 2.7: j, k, l, m, 1.92: r, 3.4: p, 4.0 to 5.7: i, n, q, 5.6: s, 6.1: t, 6.5: o.

Example 3

To 102.6 g of toluene, were added 39.0 g (0.423 mol) of 1,2,3-propanetriol and 0.36 g of dibutyltin dilaurate (DBTDL). Next, 300.1 g (1.25 mol) of 1,1-bis(acryloyloxymethyl)ethyl isocyanate was added dropwise to the reaction mixture while stirring, and the mixture was stirred for 3 hours. After checking elimination of 1,1-bis(acryloyloxymethyl)ethyl isocyanate by GC, the reaction was terminated. The obtained amount of the product was 265.3 g (93.2% yield).

Then, 249.7 g (0.438 mol) of the isolated product was dissolved in 300 g of a mixed solvent of HCFC-225ca/HCFC-225cb (ASAHICLEAN AK-225, manufactured by ASAHI GLASS CO., LTD.). After that, 37.90 g (0.902 mol) of NaF was added. Subsequently, 313.0 g (0.314 mol) of a fluorine-containing polyether acid fluoride was added dropwise to the reaction mixture while stirring, and the mixture was stirred for 5 hours. After checking elimination of a peak of acid fluoride by NMR, the reaction was terminated. The obtained amount of the product was 442.9 g (91.2% yield), and the purity was 97.2%.

The reactions in Example 3 involve the following two chemical equations.

[Chemical Equation 16]

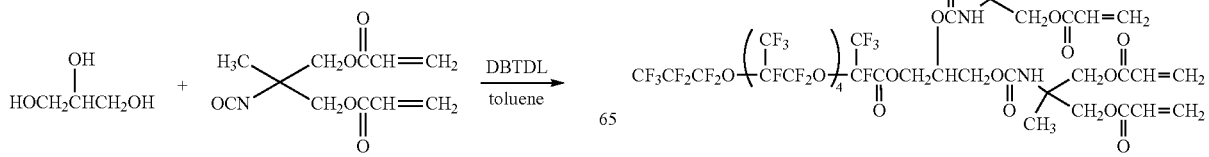

[Chemical Equation 17]

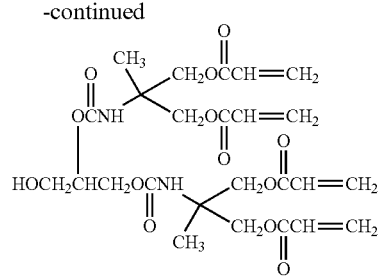

The identification results of NMR with respect to the product of Example 3 are described below. It was demonstrated that the above reactions of Example 3 yielded a carboxylic acid ester/carbamate having the following chemical formula.

[Chemical Equation 18]

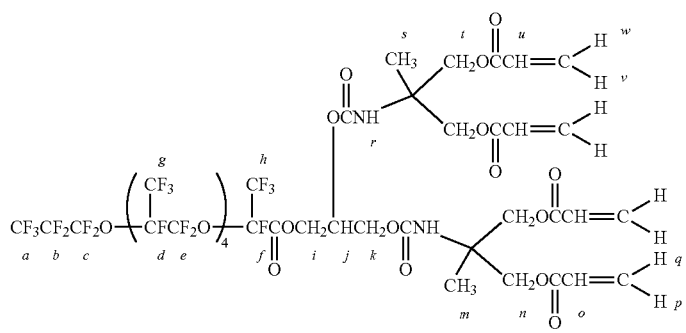

$^{19}$F-NMR[(CD$_3$)$_2$CO, C$_6$F$_6$] δ (ppm): −143,9: d, −130.2: f, −128.6: b, −84.3 to −76.3: a, c, e, g, h.
$^1$H-NMR[(CD$_3$)$_2$CO] δ (ppm): 1.5: m, s, 3.8 to 4.3: i, j, k, 4.4: n, t, 5.9: q, w, 6.2: p, v, 6.4: o, u, 6.5:1, r.

Example 4

To 101.8 g of toluene, were added 69.4 g (0.518 mol) of 1,2,6-hexanetriol and 0.44 g of dibutyltin dilaurate (DBTDL). Next, 300.0 g (1.25 mol) of 1,1-bis(acryloyloxymethyl)ethyl isocyanate was added dropwise to the reaction mixture while stirring, and the mixture was stirred for 3 hours. After checking elimination of 1, 1-bis(acryloyloxymethyl)ethyl isocyanate by GC, the reaction was terminated. The obtained amount of the product was 318.6 g (92.3% yield).

Then, 273.8 g (0.447 mol) of the isolated product was dissolved in 300 g of a mixed solvent of HCFC-225ca/HCFC-225cb (ASAHICLEAN AK-225, manufactured by ASAHI GLASS CO., LTD.). After that, 37.88 g (0.902 mol) of NaF was added. Subsequently, 306.0 g (0.307 mol) of a fluorine-containing polyether acid fluoride was added dropwise to the reaction mixture while stirring, and the mixture was stirred for 5 hours. After checking elimination of a peak of the acid fluoride by NMR, the reaction was terminated. The obtained amount of the product was 443.4 g (90.9% yield), and the purity was 96.2%.

The reactions in Example 4 involve the following two chemical equations.

[Chemical Equation 19]

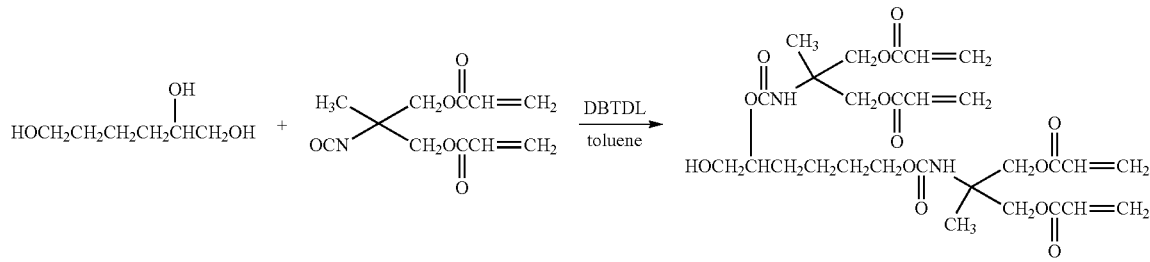

[Chemical Equation 20]

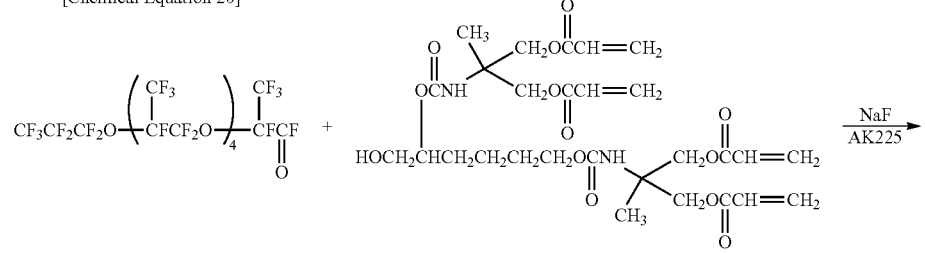

-continued

[Chemical structure image omitted]

The identification results of NMR with respect to the product of Example 4 are described below. It was demonstrated that the above reactions of Example 4 yielded a carboxylic acid ester/carbamate having the following chemical formula.

[Chemical Equation 21]

[Chemical structure image omitted]

$^{19}$F-NMR[(CD$_3$)$_2$CO, C$_6$F$_6$] δ (ppm): −143.9: d, −130.3: f, −128.5: b, −82.3 to −76.4: a, c, e, g, h.
$^1$NMR[(CD$_3$)$_2$CO] δ (ppm): 1.4: p, v, 1.5 to 1.8: k, l, m, 3.7 to 4.3:1, i, j, n, 4.8: q, w, 5.9: t, z, 6.2: s, y, 6.3 to 6.5: o, r, u, x.

The invention claimed is:
1. A carboxylic acid ester/carbamate compound having a polymerizable functional group and a fluorine atom group and represented by general formula [I]:

$$C_aF_{2a+1}O\text{—}(C_bF_{2b}O)_c\text{—}C_2F_4COO\text{—}Z\text{—}(CONHR)_d \quad [I]$$

where a is an integer of 1 to 3; b is an integer of 1 to 4; c is an integer of 0 to 50; d is an integer of 1 to 3;
Z is a divalent to tetravalent organic linking group derived from a peroxide-free alcohol represented by —(C$_e$H$_{2e}$O)$_f$—, —CH$_2$(cyclo-C$_g$H$_{2g-2}$)CH$_2$O—, or —C$_h$H$_{2h+1-i}$O$_i$—; where e is an integer of 1 to 6; f is an integer of 1 to 12; g is an integer of 3 to 6; h is an integer of 2 to 12; i is an integer of 1 to 3; and
R is a polymerizable functional group represented by general formula [II]:

$$H_2C\text{=}C(R^1)COOCH_2CR^2R^3\text{—} \quad [II]$$

where R$^1$ is hydrogen or methyl; R$^2$ is hydrogen or CH$_2$=CHCOOCH$_2$—; and R$^3$ is hydrogen or methyl.

2. A method for manufacturing a carboxylic acid ester/carbamate, comprising the steps of:
making an isocyanate compound having a polymerizable functional group and represented by general formula [IV] react with a polyalkylene glycol represented by general formula [III-1], a cycloalkane dimethanol represented by general formula [III-2], or a linear or branched polyhydric alcohol represented by general formula [III-3] to produce a hydroxycarbamate represented by general formula [V-1], [V-2], or [V-3]; and
making the hydroxycarbamate react with a perfluoropolyether carboxylic acid halide represented by general formula [VI],
wherein the general formulae are:

$$HO(C_eH_{2e}O)_fH \quad [III\text{-}1]$$

$$HOCH_2(\text{cyclo-}C_gH_{2g-2})CH_2OH \quad [III\text{-}2]$$

$$HOC_hH_{2h+1-i}(OH)_i \quad [III\text{-}3]$$

where e is an integer of 1 to 6; f is an integer of 1 to 12; g is an integer of 3 to 6; h is an integer of 2 to 12; and i is an integer of 1 to 3;

$$H_2C\text{=}C(R^1)COOCH_2CR^2R^3\text{—}NCO \quad [IV]$$

where R$^1$ is hydrogen or methyl; R$^2$ is hydrogen or CH$_2$=CHCOOCH$_2$—; and R$^3$ is hydrogen or methyl;

$$HO(C_eH_{2e}O)_fCONHR \quad [V\text{-}1]$$

$$HOCH_2(\text{cyclo-}C_gH_{2g-2})CH_2OCONHR \quad [V\text{-}2]$$

$$HOC_hH_{2h+1-i}(OCONHR)_i \quad [V\text{-}3]$$

where e is an integer of 1 to 6; f is an integer of 1 to 12; g is an integer of 3 to 6; h is an integer of 2 to 12; i is an integer of 1 to 3; and R is a polymerizable functional group represented by the following general formula [II]:

$$H_2C\text{=}C(R^1)OCOOCH_2CR^2R^3\text{—} \quad [II]$$

where $R^1$ is hydrogen or methyl; $R^2$ is hydrogen or $CH_2$=$CHCOOCH_2$—; and $R^3$ is hydrogen or methyl; and $$C_aF_{2a+1}O—(C_bF_{2b}O)_c—C_2F_4CO—X \quad\quad [VI]$$

where X is a halogen atom; a is an integer of 1 to 3; b is an integer of 1 to 4; and c is an integer of 0 to 50.

3. The method for manufacturing a carboxylic acid ester/carbamate according to claim 2, wherein an organometallic catalyst or a basic catalyst is used when the isocyanate compound having a polymerizable functional group and represented by general formula [IV] reacts with the polyalkylene glycol represented by general formula [III-1], the cycloalkane dimethanol represented by general formula [III-2], or the polyhydric alcohol represented by general formula [III-3].

4. The method for manufacturing a carboxylic acid ester/carbamate according to claim 3, wherein an organometallic tin derivative or a nitrogen-containing heterocyclic derivative is used as the organometallic catalyst or the basic catalyst.

5. The method for manufacturing a carboxylic acid ester/carbamate according to claim 2, wherein the reaction of the hydroxycarbamate represented by general formula [V-1], [V-2], or [V-3] with the perfluoropolyether carboxylic acid halide represented by general formula [VI] is carried out under the presence of a hydrogen halide scavenger.

6. The method for manufacturing a carboxylic acid ester/carbamate according to claim 5, wherein an alkali metal fluoride is used as the hydrogen halide scavenger.

* * * * *